US008623659B2

(12) United States Patent
Randolph

(10) Patent No.: US 8,623,659 B2
(45) Date of Patent: Jan. 7, 2014

(54) SICKLE CONFIRM MODIFIED HEMOGLOBIN SOLUBILITY TEST

(75) Inventor: Tim R. Randolph, Collinsville, IL (US)

(73) Assignee: Saint Louis University, St. Louis, MO (US)

( * ) Notice: Subject to any disclaimer, the term of this patent is extended or adjusted under 35 U.S.C. 154(b) by 52 days.

(21) Appl. No.: 13/238,272

(22) Filed: Sep. 21, 2011

(65) Prior Publication Data

US 2012/0077218 A1 Mar. 29, 2012

Related U.S. Application Data

(60) Provisional application No. 61/386,324, filed on Sep. 24, 2010.

(51) Int. Cl.
G01N 33/72 (2006.01)
G01N 33/48 (2006.01)
G01N 21/63 (2006.01)
C12Q 1/02 (2006.01)

(52) U.S. Cl.
USPC ............ 436/66; 436/63; 436/70; 436/164; 436/166; 436/174; 436/177; 422/430; 422/533; 422/534; 422/82.05; 422/82.09; 435/29

(58) Field of Classification Search
USPC ............ 436/63, 66, 70, 164, 166, 174, 177, 436/178; 422/430, 68.1, 533, 534, 82.05, 422/82.09; 435/29
See application file for complete search history.

(56) References Cited

U.S. PATENT DOCUMENTS

| 2,171,961 | A | * | 9/1939 | Fortune | 436/95 |
| 3,492,095 | A | * | 1/1970 | Tillen | 436/66 |
| 3,761,226 | A | | 9/1973 | Louderback et al. | |
| 3,847,545 | A | | 11/1974 | Shanbrom et al. | |
| 3,918,905 | A | * | 11/1975 | Warren et al. | 436/66 |
| 5,514,592 | A | * | 5/1996 | Schoener et al. | 436/66 |

OTHER PUBLICATIONS

Huntsman et al. Journal of Clinical Pathology, vol. 23, 1970, pp. 781-783.*
Sunderman. Abstract from Hemoglobin, Precursors, Metab. , 1964, pp. 109-110.*
Randolph, Tim R: "Determining the Usefulness of the Modified Hemoglobin Solubility Test in Diagnosing Infants with Homozygous Sickle Cell Anemia" Clinical Laboratory Science: Journal of the American Society for Medical Technology Summer 2008, vol. 21, No. 3 Jun. 2008, pp. A2, A3-A129, 141, XP002665025, ISSN: 0894-959X Retrieved from Internet: URL:http://www.ascls.org/resource/resmgr/Value-Publications/CLS_Vol_21_3_2008_final.pdf.pdf [retrieved on Dec. 2, 2011] the whole document.

(Continued)

Primary Examiner — Maureen Wallenhorst
(74) Attorney, Agent, or Firm — Randolph Bretton; The Law Office of Randolph Bretton

(57) ABSTRACT

The present invention provides a method for determining sickle-cell zygosity in a subject. The method involves forming a first solution which includes a sample from the subject, a phosphate buffer, a detergent, and a reducing agent and subjecting the first solution to centrifugation to form a second solution and a supernatant; and taking a color reading of the supernatant and of the second solution; optionally filtering the second solution to form a filtrate and a precipitate, and optionally measuring the amount of the precipitation and the absorbance of the filtrate or taking a color reading of the filtrate.

17 Claims, 3 Drawing Sheets

(56) References Cited

OTHER PUBLICATIONS

Randolph, Tim R.: "Estimated Prevalence of Sickle Cell in Northern Haiti.", Clinical Laboratory Science: Journal of American Society for Medical Technology Spring 2010 LNKD-PUBMED: 20499530, vol. 23, No. 2, Apr. 2010, pp. 79-83, XP009154550, ISSN: 0894-959X the whole document.

Anonymous: "Sickle-STAT: A Qualitative Test Kit for the Determination of the Presence of Hemoglobin S in Human Blood", Chembio Diagnostic Systems, Inc. Internet, May 1, 2006, pp. 1-3, XP002665027, Retrieved from the Internet: URL:http://www.surecheck.com/pdfs/6172%20Sickle-STAT%20SC%20901%20Product%20Insert%20Rev%203.pdff [retrieved on 2011-012-02] the whole document.

European Patent Office (International Searching Authority), International Search Report and Written Opinion for PCT/US2011/052476 (filed Sep. 21, 2011); Date of Mailing: Jan. 17, 2012.

* cited by examiner

SICKLE CONFIRM MODIFIED HEMOGLOBIN SOLUBILITY TEST

CROSS REFERENCES TO RELATED APPLICATIONS

The Present Application claims the benefit of priority from U.S. Provisional Patent Application No. 61/386,324 entitled "MODIFIED HEMOGLOBIN SOLUBILITY TEST" and filed on 24 Sep. 2010, the contents of which are hereby incorporated by reference in their entirety to the extent permitted by law.

BACKGROUND

The statements in this section merely provide background information related to the present disclosure and may not constitute prior art.

Sickle cell disease (SCD) is caused by an abnormal type of hemoglobin called hemoglobin S (Hgb S). Hemoglobin is a protein inside red blood cells that carries oxygen. When oxygen is reduced inside the red blood cell, hemoglobin S molecules will polymerize forming long thin rods, elongating the red blood cell forming the sickle cell shape. The sickle-shaped cells deliver less oxygen to the body's tissues, are removed from the blood by the spleen, and can lodge in small capillaries that disrupt blood flow resulting in anemia and painful sickle crises.

Sickle cell disease is inherited as an autosomal recessive trait, which means the disease occurs in someone who has inherited hemoglobin S from both parents. Sickle cell disease is much more common in certain ethnic groups, affecting approximately two of every thousand Blacks born in the United States. The disease is most prevalent in Africa, particularly in the sub-Saharan area. It is also observed in Haiti, the Mediterranean area, as well as India. It is characterized by general weakness and pains in muscles and joints and is fatal, frequently at an early age. Untreated, victims usually die in early childhood but many who are treated can live into middle or even late adulthood. Someone who inherits hemoglobin S from one parent and normal hemoglobin A (Hgb A) from the other parent will have sickle cell trait (SCT). Someone who inherits hemoglobin S from one parent and another type of abnormal hemoglobin, like thalassemia, from the other parent will have another form of sickle cell disease, in which patients will present with characteristics of both sickle cell and thalassemia.

Thalassemia, like sickle cell disease, is also a disorder of hemoglobin. There are many forms of thalassemia but patients with certain forms can present to a physician similarly as a patient with sickle cell disease. Thalassemia is important to the invention of the present application for two reasons. First, as previously described, patients can inherit the sickle cell abnormality and a thalassemia abnormality causing their clinical presentation and their laboratory test results to appear similar to patients with sickle cell disease. And second, certain forms of thalassemia consistently produce imbalances in the globin chains that make up hemoglobin causing excess globin chains to aggregate and precipitate inside red blood cells.

Patients with sickle cell disease need continuous treatment, even when they are not having a painful crisis. For example, patients with sickle cell disease require supplementation with folic acid, an essential vitamin necessary for cell division, because of their rapid red blood cell turnover. Children are given prophylactic antibiotic therapy to prevent potentially life-threatening infections, which are the number one cause of death in this age group. Prevention of symptoms is also accomplished by administering a drug called hydroxyurea (Hydrea) or by administering blood transfusions to keep the normal hemoglobin level (Hgb A) high and the sickle hemoglobin level (Hgb S) low. Continuous treatment or therapy serves the purpose of managing and controlling symptoms, and limiting the frequency of crises.

During a sickle crisis, certain therapies may be necessary. Moreover, treatment of pain is critical. Painful episodes may be treated with analgesics and adequate liquid intake. Non-narcotic medications may be effective, but some patients will require narcotics. Hydroxyurea was found to help some patients by reducing the frequency of painful crises and episodes of acute chest syndrome, and by decreasing the need for blood transfusions. However, there has been some concern about hydroxyurea possibly causing leukemia, though there are no definitive data that hydroxyurea causes leukemia in sickle cell patients.

While bone marrow transplants can be curative, this therapy is prescribed in only a minority of patients, predominantly because of the difficulty in finding suitable donors and the high risk of the procedure (the drugs needed to make the transplant possible are highly toxic and the new bone marrow may attack the patient's tissues). Bone marrow transplants are also much more expensive than other treatments.

Attempts are being made to develop newer drugs, which include agents that work by trying to induce the body to produce more fetal hemoglobin or by increasing the binding of oxygen to sickle cells, both of which will decrease the amount of sickling. But as yet, hydroxyurea is the only widely used drug that is available for this form of treatment. Antibiotics and vaccines are typically given to prevent bacterial infections, which are common in children with sickle cell disease. Accordingly, early diagnosis of sickle cell disease in children is essential to providing early, life-saving treatment.

The classic hemoglobin solubility testing in which sickle cell patients are identified is based on solubility differences between the normal hemoglobins A, $A_2$, and F and hemoglobin S. Hgb S results from the expression of a point mutation in the $6^{th}$ position of the beta globin chain causing the amino acid glutamic acid to be replaced with valine. The classic hemoglobin solubility test uses a mild detergent, usually Saponin, to disrupt the red blood cell (RBC) membrane and release hemoglobin into solution. A reducing agent, usually sodium hydrosulfite, is present in order to reduce the hemoglobin to the deoxygenated form, thereby altering its quaternary conformation and resultant solubility characteristics.

Normal hemoglobins (Hgb A, $A_2$, F) in the reduced state are soluble in 2.3 M phosphate buffer whereas Hgb S is insoluble. The insolubility of Hgb S produces a turbid solution that is interpreted as a positive test. Normal hemoglobins remain soluble producing a clear solution and a negative test. Unfortunately, both sickle cell heterozygotes (Hgb AS) and homozygotes (Hgb SS) produce a positive test, thereby requiring complex confirmatory testing, such as hemoglobin electrophoresis, HPLC or genetic testing, to distinguish zygosity.

DEFINITIONS

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements. The word "or" means any one member of a particular list and also includes any combination of members of that list, unless otherwise specified.

The term "about" is used herein to mean approximately, roughly, around, or in the region of. When the term "about" is used in conjunction with a numerical range, it modifies that range by extending the boundaries above and below the numerical values set forth. Preferably, the term "about" is used herein to modify a numerical value above and below the stated value by a variance of 20 percent up or down (higher or lower).

The term "amount of precipitate" is to be understood as measured using a Likert scale, as follows: "0+" corresponds to no precipitate; "1+" to a small amount of precipitate; "2+" to a moderate amount of precipitate; "3+" to a marked amount of precipitate, and "4+" to a large (maximum) amount of precipitate.

The term "filtrate" is used herein to mean a solution obtained by filtering another solution.

SUMMARY

In a first aspect, the present invention provides a method for determining sickle-cell zygosity in a subject, comprising: forming a first solution comprising a sample from the subject, a phosphate buffer, a detergent, and a reducing agent; subjecting the first solution to centrifugation to form a second solution and a supernatant; taking a color reading of the supernatant and second solution; optionally filtering the second solution to form a filtrate and a precipitate, and optionally measuring the amount of the precipitate and the absorbance of the filtrate or taking a color reading of the filtrate.

In a second aspect, the present invention provides a method for distinguishing sickle cell disease from thalassemia in a subject, comprising: forming a first solution comprising a sample from the subject, a phosphate buffer, a detergent, and a reducing agent; subjecting the first solution to centrifugation to form a second solution and a supernatant; taking a color reading of the supernatant and the second solution; optionally filtering the second solution to form a filtrate and a precipitate, and optionally measuring the amount of the precipitate and the absorbance of the filtrate or taking a color reading of the filtrate.

In a third aspect, the present invention provides a kit for determining sickle cell zygosity or distinguishing sickle cell disease from thalassemia, comprising: a detergent, a reducing agent, phosphate buffer, a color chart, and optionally one or more of: test tubes, filter paper, a hematocrit vs. volume table, a test procedure, a report form, and an interpretation guide.

DETAILED DESCRIPTION

The present invention provides a modified hemoglobin solubility test (MHST), also called "Sickle Confirm MHST," which allows for the early differentiation of sickle cell homozygous blood, sickle cell heterozygous blood, and blood not carrying the sickle cell mutation, such as normal blood or thalassemic blood, by means of a procedure involving hemolysis and color readings by visual comparison to a color chart or by absorbance spectrometry.

Accordingly, in one aspect, the invention provides a method for determining zygosity for sickle-cell anemia and separating blood samples into three groups: normal ("AA"), heterozygous sickle cell ("AS"), and homozygous sickle cell ("SS"). A sample containing hemoglobin is taken from an individual. The sample can be, for example, blood, a bodily fluid or bodily tissue. A solubility test is carried out by forming a first solution by mixing the sample or a part thereof, a phosphate buffer, a detergent, and a reducing agent to form deoxygenated hemoglobin. Deoxygenated Hgb S is insoluble in the presence of a phosphate buffer, resulting in a turbid appearance, whereas Hgb A, $A_2$ and F remain in solution.

Preferred detergents include Saponin, but any detergent that induces red cell disruption (hemolysis) without interfering with other steps of the method is acceptable. Preferred reducing agents include hydrosulfite salts, such as sodium hydrosulfite ($Na_2S_2O_4$). Example phosphate buffers can be obtained by mixing one or more of phosphoric acid and its salts, such as $K_2HPO_4$, $KH_2PO_4$, $Na_2HPO4$, and $NaH_2PO_4$. Preferably, the phosphate buffer has a concentration of 0.05 to 2.8 M, where the concentration is measured as the sum of the concentrations of species containing phosphorus. More preferably, the phosphate buffer concentration is 1.5 to 2.5 M. Most preferably, the phosphate buffer concentration is 1.7 to 2.4 M.

Figure 4:
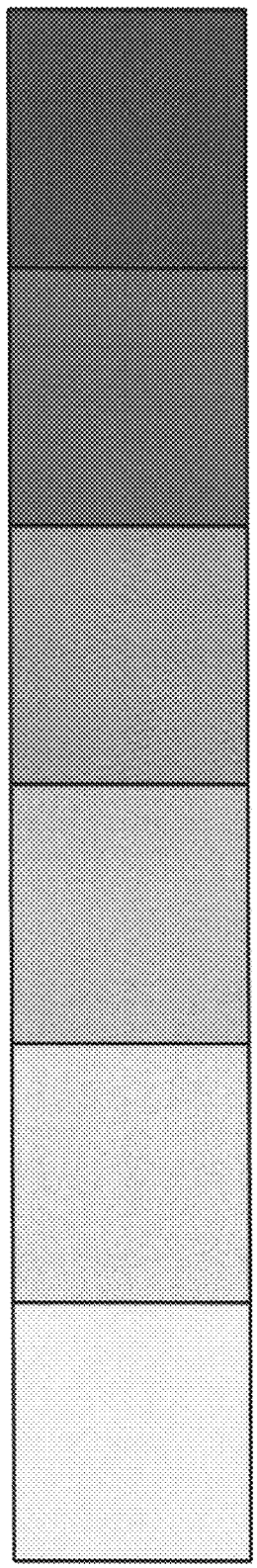
FIG. 4 shows a color chart that can be used to classify the second solution or filtrate to determine sickle cell zygosity.

The first solution is then subjected to separation of cell stroma (including membranes and organelles) and insoluble Hgb S, for instance by centrifugation, yielding a second solution and a supernatant which usually appears as a gelatinous material that rises to the surface of the second solution to form of a band. A first determination of zygosity is through a color reading of the supernatant and of the second solution. This reading may be a visual reading, optionally aided by comparing the second solution to a color chart such as that illustrated in FIG. 4. Alternatively, the reading may be carried out by means of an automated color detection apparatus.

Grayish-white supernatant can be considered a "negative" test, that is a test ruling out a "positive" (AS or SS) sample, whereas a red gelatinous supernatant band floating on top of the second solution following centrifugation can rule out an interpretation of "negative," AA hemoglobin. Without being bound to any particular theory, the grayish-white supernatant is red blood cell stroma released when red blood cells are subjected to hemolysis by the detergent, whereas the red supernatant comprises aggregates of Hgb S.

More particularly, a negative test will usually show a grayish-white supernatant on the surface of the second solution, indicating the lack of Hgb S, and the second solution will be approximately the same intensity of red as the first solution. A positive AS sample will usually show red supernatant, indicating the presence of Hgb S, and the second solution will be a significantly lighter shade of red or pink. A positive SS sample will also usually show a red supernatant, but the color of the second solution will be yellow in color with a very slight pink tinge.

The second solution is then filtered, and the absorbance of the resulting filtrate is measured, for example by means of a spectrophotometer. Filters that remove particles of 1 μm size and larger, such as Fisherbrand filter paper P5 (Fisher Scientific, Hampton, N.H.), are preferred. The absorbance is preferably measured at light frequencies in the visible spectrum (at least 390 nm to at most 750 nm). More preferred are light frequencies of at least 480 nm to at most 600 nm, and most preferred those of at least 520 nm to at most 560 nm. If a spectrophotometric apparatus or electric power is lacking, the absorbance reading can be substituted by a visual color reading of the filtrate that can be compared to a color chart such as that illustrated in FIG. 4.

Absorbance readings that are greater than about 0.700 are presumably negative for sickle cell hemoglobin, that is, the sample is presumed to contain only normal, AA, hemoglobin. However, all samples with a negative solubility test and a grayish-white band floating on top of the second solution following centrifugation should always be interpreted as being AA hemoglobin negative for sickle cell, even if the absorbance is less than 0.700. Absorbance readings between about 0.400 and about 0.700 are presumed heterozygotes, i.e. AS. However, all samples that are positive for the solubility test, show a red band floating on the surface of the second solution following centrifugation, and have an absorbance reading of greater than 0.770 should always be interpreted as heterozygous for sickle cell.

Absorbance readings of less than about 0.400 are presumed homozygotes. Most homozygous samples will show an absorbance of less than 0.300, and another absorbance reading should be taken on samples showing an absorbance of between 0.300 and 0.400. If the absorbance reading is again between 0.300 and 0.400, a new sample should be collected in a week and the test repeated.

In addition, the determination of zygosity can further be aided by measuring the amount of precipitate on the filter paper. Lastly, a normal hematocrit can rule out an interpretation of homozygous sickle cell hemoglobin.

In a second aspect, the present invention provides a kit for separating blood samples into three groups: normal ("AA"), heterozygous sickle cell ("AS"), and homozygous sickle cell ("SS"). The kit may also be used for distinguishing sickle cell disease from thalassemia. The kit comprises a detergent, a reducing agent, a phosphate buffer and a color chart. Optionally, the kit also comprises one or more of a hematocrit vs. volume table, a procedure guide, a report form, and an interpretation guide. Preferred detergents include Saponin, but any detergent that induces hemolysis without interfering with other steps of the method is acceptable. Preferred reducing agents include hydrosulfite salts, such as sodium hydrosulfite ($Na_2S_2O_4$). Example phosphate buffers can be obtained by mixing one or more of phosphoric acid and its salts, such as $K_2HPO_4$, $KH_2PO_4$, $Na_2HPO_4$, and $NaH_2PO_4$. Preferably, the phosphate buffer has a concentration of 0.05 to 2.8 M, where the concentration is measured as the sum of the concentrations of species containing phosphorus. More preferably, the phosphate buffer concentration is 1.5 to 2.5 M. Most preferably, the phosphate buffer concentration is 1.7 to 2.4 M. The color chart, for example that of FIG. 4, can be used to classify the second solution, or filtrate to determine sickle cell zygosity.

The kit can also comprise one or more vessels for forming, centrifuging, and taking spectrophotometric readings of solutions. Such vessels may include, for example, an anticoagulant vessel for placing a patient sample, a test tube for mixing a sample taken from a patient with the detergent, reducing agent, and phosphate buffer. A filtering means, such as filter paper, preferably capable of retaining particles of greater than 1 micrometer in size, may also be included in the kit. The filtering means is preferably configured to receive the volume of the above-described second solution therethrough, and to provide a filtrate and a precipitate therefrom.

The kit can be used with an apparatus that is capable of determining an absorbance reading of the filtrate. A beam of light comprising a wavelength of preferably about 540 nanometers is applied to the filtrate, from which the apparatus is capable of determining the light absorbance reading of said filtrate. The apparatus preferably senses transmittance of light through the filtrate, and provides a spectral transmittance curve that may be utilized in determining a light absorbance reading for the sample.

Representative Sickle Confirm MHST—Procedure

Blood is drawn from a subject in an EDTA or heparin anticoagulant tube using standard phlebotomy procedure. The test can also be performed on a capillary blood sample. The hematocrit of the sample is determined. Based on the hematocrit, the recommended blood volume to use in the Sickle Confirm MHST is found by referring to Table 1:

TABLE 1

Determining blood sample size (Hematocrit vs. Volume)

| Microhematocrit (%) | Volume of Blood Added to Tube (μL) |
|---|---|
| 14 | 84 |
| 15 | 83 |
| 16 | 82 |
| 17 | 81 |
| 18 | 79 |
| 19 | 77 |
| 20 | 76 |
| 21 | 74 |
| 22 | 73 |
| 23 | 71 |
| 24 | 70 |
| 25 | 68 |
| 26 | 66 |
| 27 | 64 |
| 28 | 63 |
| 29 | 62 |
| 30 | 60 |
| 31 | 59 |
| 32 | 57 |
| 33 | 56 |
| 34 | 54 |
| 35 | 52 |
| 36 | 50 |
| 37 | 48 |
| 38 | 47 |
| 39 | 46 |
| 40 | 45 |
| 41 | 43 |
| 42 | 42 |
| 43 | 40 |
| 44 | 39 |
| 45 | 37 |
| 46 | 36 |
| 47 | 35 |
| 48 | 34 |

A 2.3 M phosphate buffer solution with Saponin is added into a test tube, for example a 12×75 mm glass tube, which contains sodium hydrosulfite. About 4.0 mL of the Saponin/phosphate buffer solution should be added, or enough to fill to a predetermined line on the tube. The sodium hydrosulfite powder is dissolved in the phosphate buffer, for instance by inverting the tube 3-4 times. The sample blood from the anticoagulant tube is added to the test tube, and the test tube is optionally inverted 2-3 times, forming a first solution.

After about 6 minutes, the turbidity of the first solution is measured, for example by holding the tube in front of a lined card and observing for turbidity. A lack of turbidity indicates that the hemoglobin is normal, whereas a turbid solution indicates that the hemoglobin is heterozygous or homozygous for sickle cell. The sample is then centrifuged for 5 minutes at approximately 3,500 RPMs, forming a gelatinous band of supernatant that rises to the surface of a second solution. The color of the band of supernatant and the color of the second solution are recorded.

A negative test will show a grayish-white supernatant on the surface of the second solution, indicating the lack of Hgb S, and the second solution below the grayish-white supernatant will be approximately the same intensity of red as the first solution. A positive AS sample will show a red band of gelatinous supernatant floating on top of the second solution, indicating the presence of Hgb S, and the second solution below the red band will be a significantly lighter shade of red or pink. A positive SS sample will also show a red band floating on the surface of the solution, but the color of the second solution below the band of material will be yellow in color with a very slight pink tinge.

Next, the second solution is filtered through filtered paper. Fisherbrand filter paper P5 folded in half, and then in half again, is preferred. The filtrate solution is poured into a tube, and the amount of precipitate that is retained in the filter paper is recorded.

A negative AA sample will show no red precipitate on the filter paper and the filtrate will be the same intensity of red as the first solution and as the second solution following centrifugation. Note: A negative sample does not require the filtration step if the original solubility test is negative and the material floating on the surface of the second solution following centrifugation is grayish-white (not red).

A positive AS sample will show a moderate amount of red precipitate on the filter paper and the filtrate will be the same shade of pink as the supernatant following centrifugation. A positive SS sample will show a marked amount of red precipitate on the filter paper and the filtrate will be same shade of yellow with a tinge of pink as the supernatant following centrifugation.

The absorbance of the filtrate is then measured at the wavelength of 540 nm. Preferably, the absorbance is set at 0.00 using as blank a solution containing the phosphate buffer with Saponin and sodium hydrosulfite.

Absorbance readings will fall into one of three groups corresponding to the genotype of the patient. Absorbance readings that are greater than about 0.700 are presumably negative for sickle cell (normal AA). However, all samples with a negative solubility test and a grayish-white band floating on top of the second solution following centrifugation should always be interpreted as normal AA even if the absorbance is less than 0.700.

Absorbance readings between about 0.400 and about 0.700 are presumed heterozygotes AS. However, all samples that are positive for the solubility test and show a red band floating on the surface of the second solution following centrifugation and have an absorbance reading of more than 0.770 should always be interpreted as heterozygous for sickle cell AS.

Absorbance readings of less than about 0.400 are presumed homozygotes. Most homozygous samples will show an absorbance of less than 0.300, so all samples showing an absorbance of between 0.300 and 0.400 should be repeated on the same sample. If the absorbance reading is again between 0.300 and 0.400, a new sample should be collected in a week and the test repeated.

These diagnostic readings are reliable for patients who are greater than 1 year of age and who have not underwent treatment that would alter their hemoglobin distributions such as transfusion or hydroxyurea therapy. Testing can begin as early as 6 months of age for babies suspected of having sickle cell but results must be interpreted with care until the age of 1 year.

EXPERIMENTAL EXAMPLE

The above representative Sickle Confirm MHST procedure was carried out on 137 "treated" and "untreated" blood samples. The terms "treated" and "untreated" refer to the patients from which the samples were taken. In the United States, sickle cell is routinely diagnosed in infancy so treatment begins shortly after diagnosis. When the treatment includes blood transfusions, Hgb A is added to the patient's blood, whereas a treatment including hydroxyurea results in the adding of Hgb F to the blood. Thus, treatment can result in Hgb A or Hgb F being added to blood samples. If a patient with SS were treated with a transfusion or hydroxyurea (which is to be expected in the United States), an SS patient will look like an AS patient using the Sickle Confirm MHST—Sickle Confirm. The Sickle Confirm MHST would then be accurately measuring the Hgb S and non-Hgb S in the blood sample but misrepresenting the actual diagnosis in treated patients.

Figure 1:
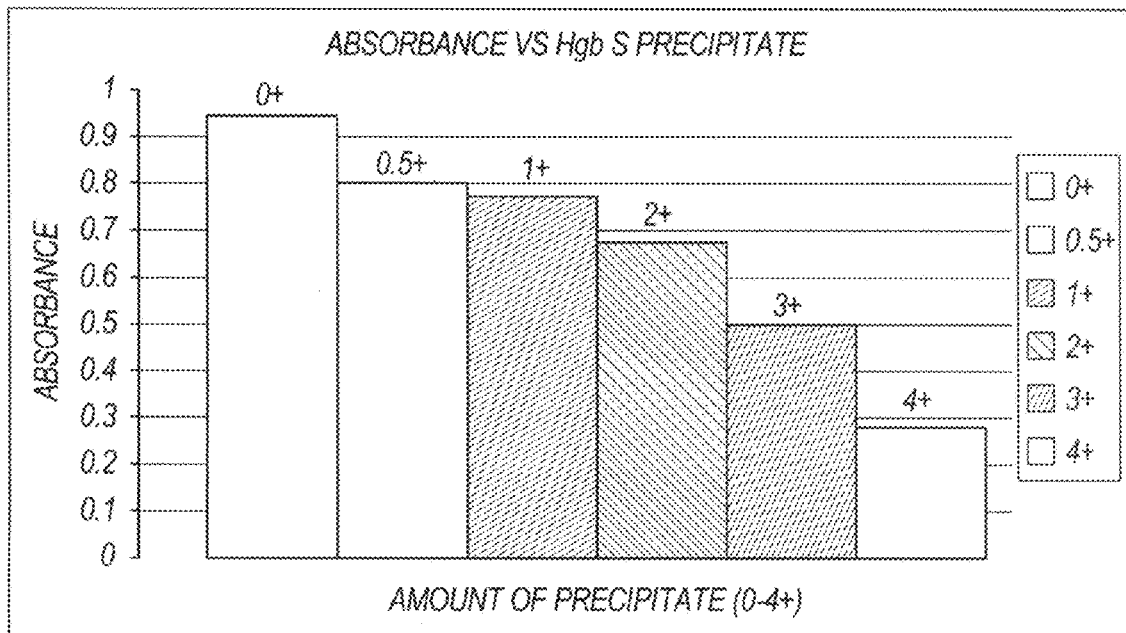
FIG. 1 is a graph showing the relationship between absorbance and amount of precipitate for 137 treated and untreated blood samples.

An inversely proportional relationship between the absorbance reading and the amount of precipitate on the filter paper was found. As the amount of precipitate on the filter paper increased, the absorbance of the filtrate went down. FIG. 1 illustrates the relationship between absorbance and amount of precipitate for 137 "treated" and "untreated" blood samples.

Figure 2:
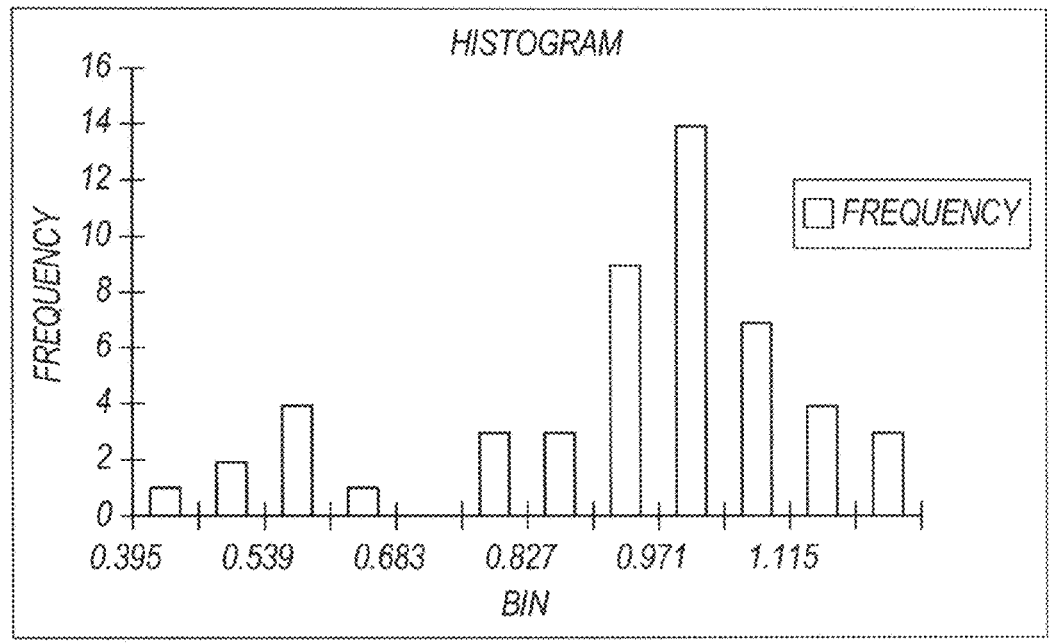
FIG. 2 shows a histogram of absorbance readings of 51 untreated Haitian blood samples.

In untreated blood samples from Haiti, more than 98% of samples fell into the expected categories. Of the 51 total samples tested, 43 produced absorbance readings of between 0.755 and 1.2 which are consistent with normal samples. There was a break in absorbance between 0.755 and 0.611. The remaining samples produced absorbance readings between 0.611 and 0.395. Only one sample (0.395) was presumably heterozygous but fell below the 0.4 threshold. FIG. 2 shows a histogram of absorbance readings of 51 untreated Haitian blood samples.

Figure 3:
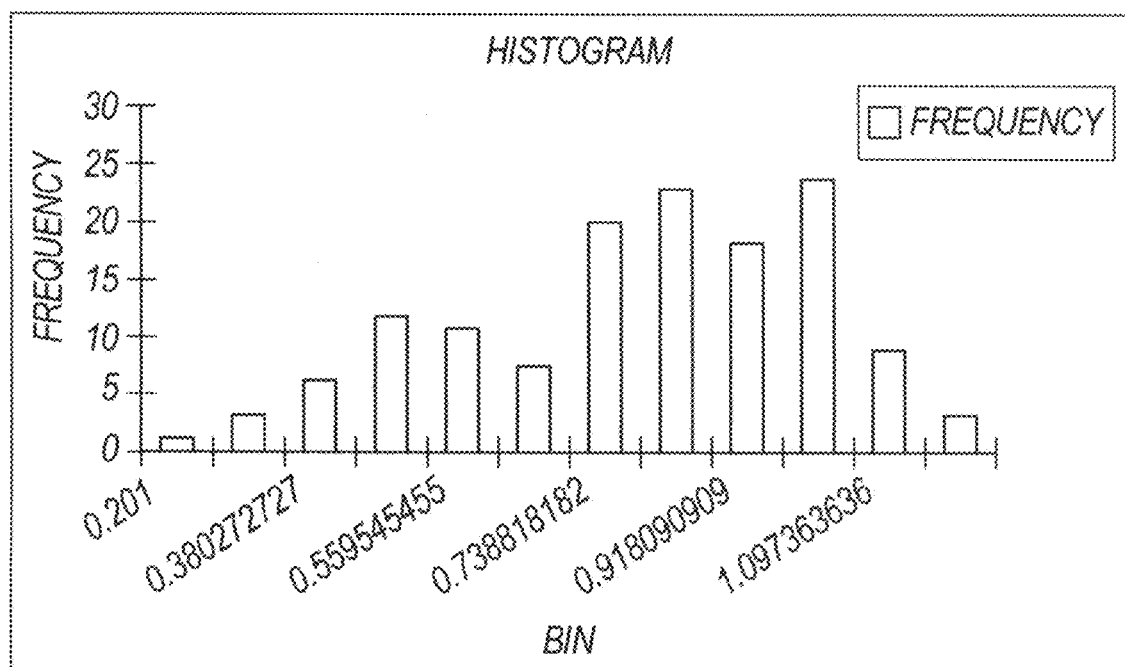
FIG. 3 shows a histogram of absorbance readings of 137 treated and untreated blood samples.

When including US samples, many of which are presumably treated, with the Haitian samples, the three absorbance groups still resolved but the breaks are less clear and there are more discrepant samples. The majority of the presumably normal samples clustered between 1.0 and 0.74. The next cluster was between 0.56 and 0.47, suggesting heterozygotes. The remaining 10 samples were all below the 0.4 threshold for a homozygous sample but 6 fell in the 0.38 bin, placing them close to the cutoff between heterozygous and homozygous. FIG. 3 shows a histogram of absorbance readings of 137 Treated and Untreated Blood Samples. The borderline and discrepant samples are explained by the effect of treatment that will shift the ratio of normal hemoglobin to sickle hemoglobin in favor of normal hemoglobin, thus increasing the absorbance readings and shifting samples upwards on the absorbance scale.

When the genotypes of samples are confirmed by hemoglobin electrophoresis, absorbance readings fall within predictable groupings to predict zygosity. Table 2 below reports the absorbance readings using the Sickle Confirm MHST of the invention versus Sickle Cell Zygosity as determined by hemoglobin electrophoresis testing. Also reported are the amounts of precipitate, measured using a Likert scale.

TABLE 2

Absorbance Readings Using the MHST vs. Sickle Cell Zygosity

| Sample # | Solubility Test | Zygosity by Electrophoresis | Absorbance | Precipitate on Filter Paper |
|---|---|---|---|---|
| Researcher | Negative | Normal | 0.966 | 0+ |
| Researcher | Negative | Normal | 0.946 | 0+ |
| SLUH5 | Positive | Heterozygote | 0.785 | 2+ |
| SLUH9 | Positive | Heterozygote | 0.785 | 1+ |
| SLUH6 | Positive | Heterozygote | 0.696 | 2+ |
| CGCH1 | Positive | Heterozygote | 0.67 | 3+ |

TABLE 2-continued

Absorbance Readings Using the MHST vs. Sickle Cell Zygosity

| Sample # | Solubility Test | Zygosity by Electrophoresis | Absorbance | Precipitate on Filter Paper |
|---|---|---|---|---|
| CGCH2 | Positive | Heterozygous | 0.658 | 2+ |
| SLUH3 | Positive | Heterozygote | 0.623 | 2+ |
| SLUH4 | Positive | Homozygote | 0.321 | 4+ |
| CGCH8 | Positive | Homozygote | 0.29 | 4+ |

Additional field testing in Haiti generated more data. A total of 176 patients underwent tests that were verified by hemoglobin electrophoresis as homozygous normal (AA), heterozygous sickle cell (AS), or homozygous sickle cell (SS). In addition, three patients were determined to be a compound heterozygous hemoglobin SC patient (SC). Table 3 summarizes the results of the Sickle Confirm MHST and compares the zygosity diagnosis of the Sickle Confirm MHST to the hemoglobin electrophoresis results.

TABLE 3

Concordance between the Sickle Confirm MHST and hemoglobin electrophoresis

Normal Samples (AA)

| N | Solubility – White Band Abs. >0.70 | Solubility – White Band Abs. <0.70 | Number of Concordant Samples | Number of Discordant Samples | Sensitivity | Specificity |
|---|---|---|---|---|---|---|
| 48 | 37 | 11 | 48 | 0 | 100% | 100% |

Heterozygous Sickle Cell Samples (AS)

| N | Solubility + Red Band Abs. >0.40 | Solubility + Red Band Abs. <0.40 | Number of Concordant Samples | Number of Discordant Samples | Sensitivity | Specificity |
|---|---|---|---|---|---|---|
| 120 | 114 | 6 | 114 | 6 | 95% | 100% |

Homozygous Sickle Cell Samples (SS)

| N | Solubility + Red Band Abs. <0.4 | Solubility + Red Band Abs. >0.4 | Number of Concordant Samples | Number of Discordant Samples | Sensitivity | Specificity |
|---|---|---|---|---|---|---|
| 8 | 8 | 0 | 8 | 0 | 100% | 100% |

In addition, three hemoglobin SC compound heterozygotes were identified and, as expected, produced absorbance readings in the low end of the heterozygous AS range and the upper end of the homozygous SS range (0.368, 0.400, 0.532).

Based on some or all of the following data: hematocrit, solubility result, color of the supernatant, color of the second solution, amount of precipitate on the filter paper and the light absorbance reading or color of the filtrate, the patient's blood sample is determined to be one of three possible categories: normal (AA), heterozygous sickle cell (AS), or homozygous sickle cell (SS). In clinic laboratories that lack electricity or a spectrophotometer, the absorbance reading can be substituted by a visual color reading of the supernatant, second solution or filtrate that can be compared to a color chart instead such as that illustrated in FIG. 4.

What is claimed is:

1. A method for determining sickle-cell zygosity in a subject, comprising:

a) determining a subject's blood hematocrit;
b) forming a first solution comprising a volume of blood from the subject, the volume of the blood determined according to the subject's hematocrit as set forth in Table 1, and 4 milliliters of a phosphate buffer, comprising a detergent, and a reducing agent;
c) determining the presence or absence of turbidity in the first solution after about 6 minutes;
d) subjecting the first solution to centrifugation to form a second solution and a supernatant the second solution comprising a band of material floating on the second solution;
e) filtering the second solution to form a filtrate and a precipitate;
f) taking a color reading of the band of material floating on the second solution, measuring the absorbance of the filtrate and determining the amount of the precipitate on a 1 to 4 Likert scale; and
g) diagnosing the subject as negative for sickle-cell if the turbidity of the first solution is absent, or the band of floating material is white, or the absorbance of the filtrate is from about 0.7 or greater, or if the amount of the precipitate is 0;
h) diagnosing the subject as heterozygous for sickle-cell if turbidity in the first solution is present, or the band of floating material is red, and either the absorbance of the filtrate is from about 0.4 to about 0.7, or if the amount of the precipitate is from 1 to 3;
i) diagnosing the subject as homozygous for sickle-cell if turbidity in the first solution is present, or the band of floating material is red, and either the absorbance of the filtrate is from about 0.4 or less or if the amount of the precipitate is 4.

2. The method of claim 1, wherein the detergent is Saponin.

3. The method of claim 1, wherein the reducing agent is sodium hydrosulfite.

4. The method of claim 1, wherein the onion concentration of the phosphate buffer is 1.7 to 2.4 M.

5. The method of claim 1, wherein the measuring the absorbance of the filtrate is at a frequency of at least 390 nm to at most 750 nm.

6. The method of claim 1, wherein the measuring the absorbance of the filtrate is at a frequency of at least 480 nm and at most 600 nm.

7. The method of claim 1, wherein the measuring the absorbance of the filtrate is at a frequency of at least 520 nm and at most 560 nm.

8. A kit for determining sickle cell zygosity, comprising: a detergent, a reducing agent, phosphate buffer, and a hematocrit vs. volume table as set forth in Table 1.

9. The kit of claim 8, further comprising a vessel for mixing the detergent, the reducing agent, the phosphate buffer, and a sample taken from a subject.

10. The kit of claim 8, further comprising a filter paper.

11. The kit of claim 8, further comprising: a color chart correlating color with sickle-cell disease, sickle-cell trait, and negative sickle-cell.

12. The kit of claim 11 wherein the color chart correlating color with sickle-cell disease, sickle-cell trait, and negative sickle-cell consists of the color chart set forth in FIG. 4.

13. A method for determining sickle-cell zygosity in a subject, comprising:

a) determining a subjects blood hematocrit;
b) forming a first solution comprising a volume of blood from the subject, the volume of the blood determined according to the subjects hematocrit as set forth in Table 1, and 4 milliliters of a phosphate buffer, comprising a detergent, and a reducing agent;

c) determining the presence or absence of turbidity in the first solution after about 6 minutes;

d) subjecting the first solution to centrifugation to form a second solution and a supernatant the second solution comprising a band of material floating on the second solution;

e) filtering the second solution to form a filtrate and a precipitate;

f) determining the color of the band of material floating on the second solution, determining the color of the filtrate, and determining the amount of the precipitate on a 1-4 Likert scale; and g) diagnosing the subject as negative for sickle-cell if the turbidity of the first solution is absent, or the band of floating material is white, or the color of the filtrate correlates with a color on a color chart that represents negative sickle cell;

h) diagnosing the subject as heterozygous for sickle-cell if turbidity in the first solution is present, or the band of floating material is red, and either the color of the filtrate correlates with a color on a color chart that represents a heterozygous sickle cell trait, or if the amount of the precipitate is from 1 to 3;

i) diagnosing the subject as homozygous for sickle-cell if turbidity in the first solution is present, or the band of floating material is red, and either the color of the filtrate correlates with a color on a color chart that represents homozygous sickle cell disease, or if the amount of the precipitate is 4.

14. The method of claim 13, wherein the detergent is Saponin.

15. The method of claim 13, wherein the reducing agent is sodium hydrosulfite.

16. The method of claim 13, wherein phosphate buffer is 1.7 to 2.4 M.

17. The method of claim 13, wherein the color chart correlated to indicate negative sickle cell, sickle cell trait, and sickle cell disease, consists of the color chart set forth in FIG. 4.

* * * * *